(12) United States Patent
Henkelmann et al.

(10) Patent No.: US 6,384,235 B2
(45) Date of Patent: May 7, 2002

(54) PREPARATION OF SUBSTITUTED INDOLES

(75) Inventors: Jochem Henkelmann; Jan-Dirk Arndt, both of Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/782,310

(22) Filed: Feb. 14, 2001

(30) Foreign Application Priority Data

Feb. 25, 2000 (DE) ......................................... 100 09 000

(51) Int. Cl.$^7$ ............................................ C07D 209/10
(52) U.S. Cl. ..................................... 548/494; 548/495
(58) Field of Search ................................ 548/494, 495

(56) References Cited

PUBLICATIONS

Utimoto et al. "Palladium Catalyzed Reaction of 2–Alkynylanilines with Allyl Chlorides. Formation of 3–Allylinkoles" Tetrahedron Letters vol. 23(1989) pp. 1799–1782.
McDonald et al. "Group VI Metal–Promoted Endo Azacyclization via Ikyne–Derived Metal Vinylidene Carbenes" Tetrahedron Letters vol. 38, (1997) pp. 7687–7690.
McDonald "Alkynol endo–Cycloisomerizations and conceptually Related Transformations" Chem. Eur. J. vol. 5, (1999) pp. 3103–3106.
Cacchi et al. "A Versatile Approach o 2,3–Disubstituted Indoles through the Palladium–Catalysed Cyclization of o–Alkynyltrifluoroacetanilides with Vinyl Triflates and Aryl Halides" Tetrahedron Letters vol. 33, (1992) pp. 3915–3918.
Cacchi et la. "2–Substituted–3–acylindoles through the Palladium–Catalysed Carbonylative Cyclization of 2–Alkynyltrifluoroacetanilides with Aryl Halides and Vinyl Triflates" Tetrahedron vol. 50, (1994) pp. 437–452.
Cacchi et al. "3–Aryl–2–Unsubstituted Indoles through the Palladium–catalysed reaction of 6–Ethynyltrifluoroacetanilide with Ary Iodides" Synlett (1977) pp. 1363–1366.
Yamanaka et al. "Facile Synthesis of 2–Substituted Indoles from o–Bromoaniline" Heterocycles vol. 24, (1986) pp. 31–32.
Cacchi et al (1988): J. Org. Chem; 63, 1001–1011.*
Villemin et al (1989): Heterocycles; 29 (7), 1255–1261.*
Ezquerra et al (1996): J. Org. Chem; 61, 5804–5812.*

* cited by examiner

Primary Examiner—Floyd D. Higel
Assistant Examiner—Golam M. M. Shameem
(74) Attorney, Agent, or Firm—Keil & Weinkauf

(57) ABSTRACT

The present application describes a process for preparing compounds of the indole type of the formula

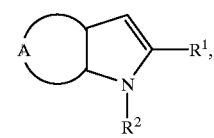

(I)

in which A is a hydrocarbon radical which, together with the carbons to which it is attached, forms a substituted or unsubstituted mono- or polycyclic aromatic system which may contain one or more heteroatoms from the group consisting of N, O and S, and $R^1$, $R^2$ independently of one another are H, a saturated, linear or branched aliphatic $C_1$–$C_{20}$-hydrocarbon radical, an unsaturated, linear or branched aliphatic $C_2$–$C_{20}$-hydrocarbon radical, a saturated or unsaturated, unsubstituted or alkyl-substituted cycloaliphatic $C_3$–$C_{20}$-hydrocarbon radical or an aromatic $C_5$–$C_{20}$-hydrocarbon radical, where these radicals may contain in their molecular skeleton one or more heteroatoms from the group consisting of the halogens, N, P, O, S, Si, Sn and B and may be substituted or unsubstituted, by cyclization of alkynylaminoaromatics of the formula

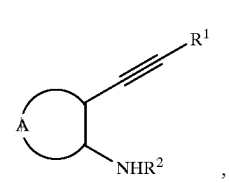

(II)

in which $R^1$ and $R^2$ are as defined in formula (I) and $R^1$, $R^2$ or A may be attached to an organic or inorganic carrier, which comprises carrying out the reaction in a polar aprotic ion-solvating solvent in the presence of a suitable compound of Na, K, Rb or Cs.

Using this process, it is possible to prepare substituted indoles in a simple manner and in high yields.

16 Claims, No Drawings

PREPARATION OF SUBSTITUTED INDOLES

The present invention relates to a process for preparing substituted indoles of the formula (I), in which substituted 2-alkynylanilines are cyclized in a polar aprotic solvent with the aid of a suitable alkali metal compound.

Simple, low-cost indole syntheses are of great general interest, since the indole structure is found in numerous natural products and in particular in pharmacologically active substances. To date, there are a number of principal routes leading to the desired indole derivatives.

Intramolecular addition of amino groups to a carbon-carbon triple bond with formation of indole derivatives is a reaction known from the literature. The reaction can be catalyzed, for example, by palladium complexes. This is described, inter alia, in the publication by K. Utimoto et al. in Tetrahedron Letters 29 (1992), 3915 ff.

Other publications disclose the use of molybdenum(0) compounds in these cyclization reactions. This can be found in the publications by F. E. McDonald et al. in Tetrahedron Letters 38 (1997), 7687 ff. and in Chem. Eur. J. 5 (1999), 3103 ff.

In a variant described in a plurality of publications by S. Cacchi et al., for example in Tetrahedron Letters 33 (1992), 3915 ff., Synlett 1997, 1393 ff., Tetrahedron Letters 50 (1994), 437 ff., it is possible to use, instead of the alkynylanilines, the corresponding trifluoroacetamides, the catalysts used here again being palladium complexes.

The synthesis of substituted indoles is furthermore described by Yamanaka et al. in Heterocycles 24 (1986), 31/32. Here, alkynylcarbanilates are cyclized in the presence of Na ethoxylate, and the N-bonded C(O)O-alkyl unit is removed by hydrolysis. This cyclization reaction does not work if the starting material used is a 2-alkynylaniline.

However, in all of these reactions it is frequently necessary to heat the reaction mixture to relatively high temperatures, and frequently, long reaction times are additionally required to achieve acceptable yields. These harsh reaction conditions, which are generally required, strongly restrict, inter alia, the range of the various functionalities which can be present in the 2-alkynylanilines.

It is an object of the present invention to provide a process which allows a simple preparation of the substituted indoles, with good yields and using short reaction times and low reaction temperatures. The process should furthermore permit the synthesis of substituted indoles having a large number of different substituents.

We have found that this object is achieved by a process for preparing compounds of the indole type of the formula

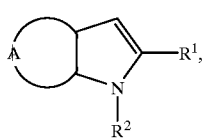
(I)

in which A is a hydrocarbon radical which, together with the carbons to which it is attached, forms a substituted or unsubstituted mono- or polycyclic aromatic system which may contain one or more heteroatoms from the group consisting of N, O and S, and
$R^1$, $R^2$ independently of one another are H, a saturated, linear or branched aliphatic $C_1$–$C_{20}$-hydrocarbon radical, an unsaturated, linear or branched aliphatic $C_2$–$C_{20}$-hydrocarbon radical, a saturated or unsaturated, unsubstituted or alkyl-substituted cycloaliphatic $C_3$–$C_{20}$-hydrocarbon radical or an aromatic $C_5$–$C_{20}$-hydrocarbon radical, where these radicals may contain in their molecular skeleton one or more heteroatoms from the group consisting of the halogens, N, P, O, S, Si, Sn and B and may be substituted or unsubstituted, by cyclization of alkynylaminoaromatics of the formula

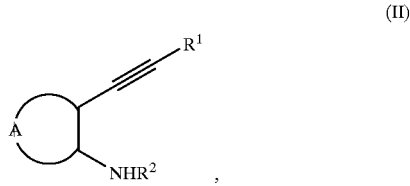
(II)

in which $R^1$ and $R^2$ are as defined in formula (I) and $R^1$, $R^2$ or A may be attached to an organic or inorganic carrier, which comprises carrying out the reaction in a polar aprotic ion-solvating solvent in the presence of a suitable compound of Na, K, Rb or Cs.

We have found that the process according to the invention permits access to a large number of compounds of the indole type of a range which has not been possible with the processes of the prior art. By using the alkali metal compounds which are employed in the process according to the invention, it is possible to prepare indole derivatives which may have virtually any customary substituents $R^1$, $R^2$. In the individual case, the accessibility of certain substituted indole derivatives depends on the influence of certain parameters. These are, for example, steric interactions between the individual substituents present, and possibly also the aromatic system is of the indole derivative. The range of the different substituents $R^1$ and $R^2$ and of the substituents which may be present on the aromatic system of the formula (I) is enormously wide and comprises virtually all compound classes and functional groups which are included in the definition given above.

In a preferred embodiment of the present invention, the substituents $R^1$ and $R^2$ independently of one another are selected from the group consisting of H, linear and branched $C_1$–$C_{12}$-alkyl groups, linear and branched $C_2$–$C_{12}$-alkenyl groups, $C_3$–$C_8$-cycloalkyl groups, $C_3$–$C_8$-cycloalkenyl groups, $C_5$- and $C_6$-heterocycles having one or more ring atoms selected from the group consisting of N, O and S and mono- or bicyclic aromatics having one or more ring atoms selected from the group consisting of N, O and S.

Both in the preferred and the not preferred embodiments, the substituents $R^1$ and $R_2$ may have one or more substituents in their molecular skeleton.

Examples of preferred substituents are amino and nitro groups, halogens, hydroxyl and ether groups, thiol groups, thioether groups, amide and ester groups, sulfaryl groups and sulfoxide groups.

The aromatic system in the compounds of the formula (I) can be a mono- or polycyclic aromatic which comprises exclusively carbon and hydrogen or which may have one or more heteroatoms selected from the group consisting of N, O and S.

The aromatic system is preferably a mono- or bicyclic aromatic. More preferably, the aromatic system is a $C_5$-heterocycle or a benzene or naphthalene derivative which may contain one or more of the heteroatoms N, O and S mentioned, examples being benzene and naphthalene, aza-, diaza- and triazabenzene, aza-, diaza- and triazanaphthalene, thiophene and furan.

In the most preferred embodiment of the present invention, the aromatic system in the formula (I) is selected from the group consisting of benzene, naphthalene, pyridine, pyrazine, pyrimidine, quinoline, thiophene and furan.

Both in the preferred and the not preferred embodiments, the aromatic system may have one or more substituents which, similarly to the substituents $R^1$ and $R^2$, may vary extremely. Non-limiting examples of such substituents are alkanes and alkenes which are either unsubstituted or may carry customary substituents, for example halogens, amines, nitro groups, ether and hydroxyl groups or thiol- and thioether groups. Further examples of substituents on the aromatic system are amino and nitro groups, halogens, hydroxyl and ether groups, thiol groups, sulfaryl groups, sulfoxide groups, thioether groups, amide and ester groups.

In one embodiment of the present invention, the synthesis of the indole derivatives (I) can be carried out by attaching the alkynylaminoaromatic (II) used as starting material to an organic or inorganic carrier and immobilizing it. These carriers are known to the person skilled in the art and correspond to the customary carrier materials used, for example, for solid-phase peptide synthesis or for fixing transition metal catalyst systems. Examples are Merrifield resin, 4-(2', 4'-dimethoxyphenyl-Fmoc-aminomethyl)-phenoxyacetamido-norleucyl-methylbenzhydrylamino-(divinylbenzene-crosslinked polystyrene) resin, also known under the name Rink-MBHA resin, which is generally used after deprotection by removal of the 9-fluorenylmethoxycarbonyl-(Fmoc) group, and the carrier resin which is commercially available under the name trityl chloride resin, if appropriate after appropriate modification.

These carriers are either bonded to the aromatic system of the starting materials (II), or the substituent $R^1$ is attached to the carrier. If appropriate, the carrier may have suitable spacer groups which are attached to the starting material. Following the synthesis of the corresponding indole compound, the bond between the carrier and the target molecule is broken in a customary manner known to the person skilled in the art, for example by cleaving the bond between carrier and spacer group using trifluoroacetamide.

A further embodiment of the present invention allows the synthesis of compounds (I) in which the aromatic system, which is fused with the pyrroline unit, forming a bicyclic indole unit, is fused with a further pyrroline unit, forming a tricyclic bifunctional indole. To this end, the starting material (II) used is a compound which does not only have one acetylene function and one amino function in a vicinal position, but in each case two of these functions.

The synthesis element according to the invention can also be widened such that the resulting indole does not only contain 2 pyrroline units, but 3 or even more of these units. To this end, a starting material (It) is used which contains 3 or even more vicinal acetylene and amino functions.

The synthesis according to the invention is carried out using a suitable compound of Na, K, Rb or Cs, which is employed in combination with a polar aprotic solvent having ion-solvating properties. By using these solvents, it is possible to increase the electrophilicity of the ions of the metals mentioned such that the cyclization according to the invention can be carried out under mild conditions.

These polar aprotic ion-solvating solvents are known to the person skilled in the art, examples being N-methylpyrrolidone (NMP), N-butylpyrrolidone (NBP), dimethyl sulfoxide (DMSO), sulfolane (tetrahydrothiophene 1,1-dioxide), dimethylformamide (DMF), tetrahydrofuran (THF), ethers, hexamethylphosphoric triamide (HMPT) and N,N'-dimethylpropyleneurea.

Examples of suitable ethers are ethers which can be obtained from ethylene oxide and/or propylene oxide. This can be ethylene glycol and propylene glycol ethers, oligo- or polyethylene glycol, oligo- and polypropylene glycol and ethylene glycol/propylene glycol copolymers or block copolymers, such as, for example, the compounds known under the names glyme, diglyme, triglyme or the names Pluronic® and Pluriol® (from BASF AG). It is also possible to use ethers which are prepared by condensing ethylene oxide and/or propylene oxide with polyvalent amines, for example the products available under the names Tetronic® and Lutensol® (in each case from BASF AG).

It is also possible to use the respective ethers, for example the methyl ethers, of all of the abovementioned ethylene glycol and propylene glycol ethers, which, for example in the case of Pluronic®, Pluriol® and Tetronic®, may still have free terminal hydroxyl groups. Suitable ethers are also crown ethers and cryptands.

These solvents can be used on their own, as a mixture or as additive to other solvents. They have to be added in an amount which is sufficient to achieve the desired ion solvation and thus the required reactivity.

The compounds of Na, K, Rb and Cs which are employed are those which dissociate well in the solvents mentioned and whose ions are sufficiently solvated by these solvents. Examples of suitable compounds of the alkali metals quoted are hydroxides, hydrides, alkoxides, amides and aminopropylamides.

Particularly suitable compounds are hydroxides and alkoxides.

Among the abovementioned metals Na, K, Rb and Cs, the best reactivities are obtained when K and Cs are used, and their use is preferred. The alkali metal compounds used according to the invention can be employed in stoichiometric or superstoichiometric amounts, but also in catalytic amounts. The minimum amount of alkali metal compounds is about 5 mol %; however, it is also possible to use amounts of up to 250 mol %, based on the substrate. The reaction temperatures required for the process according to the invention are about <100° C. The process according to the invention is preferably carried out at temperatures of about 20–60° C., most preferably of about 20–40° C. The reaction times are from about 2 to 20 hours, preferably from 2 to 8 hours. The starting materials (II) are obtained by the Sonogashira reaction (see K. Sonogashira et al., Synthesis 1980, 627 ff., K. Sakomoto, Synthesis 1983, 312 ff., G. C. Fu et al., Angew. Chem. Int. Ed. Engl. 38 (1999), 2411 ff.) from the corresponding 2-iodo- or 2-bromoanilines by reaction with 1-alkynes. If the process according to the invention is carried out on a carrier, in solid phase, the corresponding iodo- or bromoaniline is, prior to the Sonogashira coupling, fixed to the carrier using methods known to the person skilled in the art. The invention is now illustrated by the examples below.

EXAMPLE 1

Synthesis of 2-phenylindole using different alkali metal compounds

A solution of 1.05 mmol of the alkali metal compound in question was dissolved or suspended under argon in 4 ml of NMP. 97 mg (0.5 mmol) of 2-phenylethynylaniline in 1 ml of NMP were then added. The solution was then stirred vigorously at the temperatures given in Table 1, for the stated reaction times. 1 ml of water and 50 ml of dichloromethane were then added, and the resulting solution was washed with a saturated NaCl solution. The solution was dried over $MgSO_4$, the residue was filtered off, the solution was concentrated under reduced pressure and the resulting residue was then purified chromatographically on a silica gel column using a $CH_2Cl_2$/pentane mixture. Removal of the solvent gave the pure product.

The results are shown in Table 1. The stated yields are based on analytically pure end product.

TABLE 1

| Experiment | Base | Temp. [° C.] | Time [h] | Yield [%] |
|---|---|---|---|---|
| A | NaH | 60 | 8 | >5 |
| B | NaOEt | 80 | 15 | 66 |
| C | KOt-Bu | 25 | 4 | 79 |
| D | KH | 25 | 5 | 72 |
| E | CsOH | 90 | 5 | 68 |
| F | CsOt-Bu | 25 | 5 | 71 |

EXAMPLE 2

Synthesis of different indole and azaindole derivatives

Method A

Under argon, 0.5 mmol of the starting material in question is added to a stirred solution of 42 mg (1.05 mmol) of KH in 4 ml of NMP. After 3 to -12 hours at room temperature, the reaction solution was worked up as in Example 1. The results are shown in Table 2.

Method B

The reaction was carried out as described under A, using the alkali metal compound KOt-Bu. The reaction time was 4 hours at room temperature. Work-up, too, was carried out as described in Example 1. The results are also shown in Table 2.

TABLE 2

| Experiment | Aniline used | Indole derivative obtained | Method | Yield [%] |
|---|---|---|---|---|
| 1 | 1a; R = Ph | 2a: R = Ph | A(B) | 72(79) |
| 2 | 1b: R = Bu | 2b: R = Bu | A(B) | 76(78) |
| 3 | 1c: R = 1-cyclohexenyl | 2c: R = 1-cyclohexenyl | A | 67 |
| 4 | 1d: R = H | 2d: R = H | B | 62 |
| 5 | 1e: R = (CH$_2$)$_2$OH | 2e: R = (CH$_2$)$_2$OH | A | 61 |
| 6 | 1f: R = CH(OEt)$_2$ | 2f: R = CH(Oet)$_2$ | B | 81 |
| 7 | 1g: R2-thienyl | 2g: R = 2-thienyl | A | 70 |
| 8 | 1h: R = 2-thiazole | 2h: R = 2-thiazole | A | 61 |
| 9 | 1i: R3-chloropropyl | 2i: R = 3-cyclopropyl | A | 75 |
| 10 | 1j: R = 2-aminophenyl | 2j: R = 2-aminophenyl | A | 82 |
| 11 | 1k | 2k | A | 80 |
| 12 | 1l | 2l | B | 77 |

TABLE 2-continued
| Experiment | Aniline used | Indole derivative obtained | Method | Yield [%] |
|---|---|---|---|---|
| 13 | 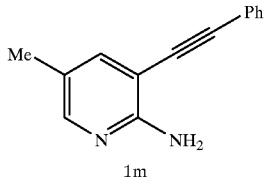 1m |  2m | A | 72 |
| 14 | 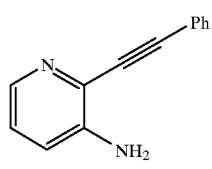 1n | 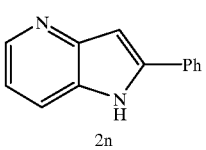 2n | A | 74 |
| 15 | 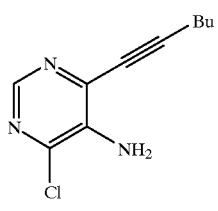 1o | 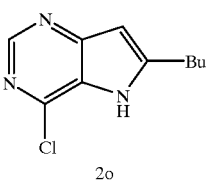 2o | B | 78 |
| 16 | 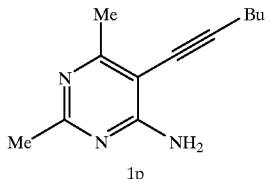 1p | 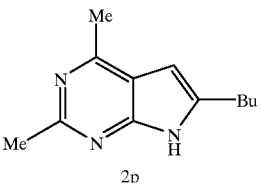 2p | B | 61[a] |
| 17 | 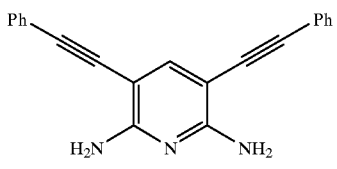 1q | 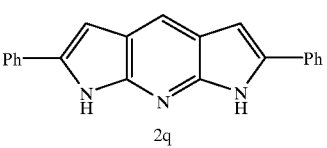 2q | B | 80[b] |
| 18 | 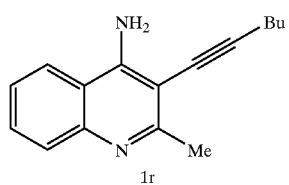 1r | 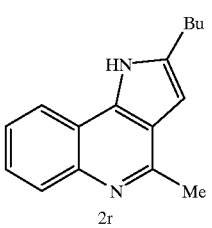 2r | B | 90[b] |
[a] 60° C./5 h
[b] 80° C./6 h

EXAMPLE 3
Solid-phase synthesis of substituted indoles

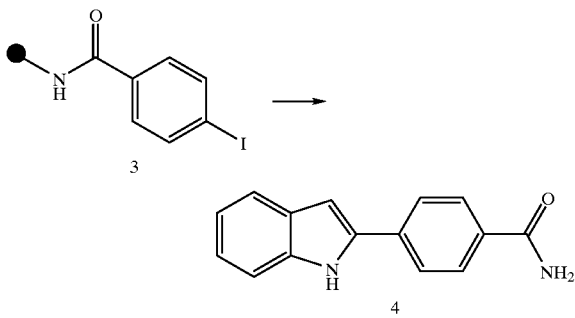

a) preparation of starting material 3

Deprotected Rink-MBHA resin (2 g; 0.64 mmol/g, obtainable by reaction of Rink-MBHA resin with piperidine, was, in a shaker glass fitted with septum and filled with argon, swollen for about 10 min in dichloromethane (15 ml) and then admixed with 4-iodobenzoic acid (478 mg; 1.92 mmol) and N,N'-diisopropylcarbodiimide (DIC) (240 mg; 1.92 mmol). The suspension was shaken at room temperature for 20 h. The polymer was filtered and washed alternately with dichloromethane, methanol, THF and DMF (in each case about 15 ml). The washing procedure was repeated three times. The polymer was then washed four times with dichloromethane (in each case about 15 ml) and dried at 55° C. for about 16 h.

b) The resulting product was then subjected to two successive Sonogashira couplings, the cyclization according to the invention and cleavage from the polymer resin.

To this end, in the first coupling, polymer-bound 4-iodobenzamide (500 mg; 0.25 mmol), Pd(PPh$_3$)$_2$Cl$_2$ (17.4 mg; 0.025 mmol) and CuI (11.8 mg; 0.062 mmol) were initially charged in a Schlenk tube, fitted with septum and filled with argon, and swollen in toluene (5 ml) for about 10 min. Diethylamine (5 ml) was then added, the mixture was cooled to 0° C. and trimethylsilylacetylene (245 mg; 2.5 mmol) was added. The mixture was stirred at room temperature for 12 h and the polymer was then filtered and washed with DMF, methanol and THF (in each case about 10 ml). The washing procedure was repeated four times. The polymer was then washed four times with dichloromethane (in each case about 10 ml) and then admixed with TBAF (5 ml; 0.25 M in THF) and shaken for about 15 min. The resin was washed as described above and dried at 55° C. for about 16 h.

The second coupling was carried out like the first coupling, including washing procedure and drying.

The following amounts were used:

Resin-bonded 4-ethynylbenzamide (400 mg; 0.22 mmol); Pd(PPh$_3$)$_2$Cl$_2$ (15.4 mg; 0.022 mmol); CuI (10.5 mg; 0.055 mmol); toluene (4 ml); diethylamine (4 ml); 2-iodoaniline (450 mg; 2.2 mmol).

The resulting resin-bound amino-substituted diphenylacetylene can also be obtained in one step from the resin-bound 4-iodobenzamide and 2-trimethylsilylethynylaniline. This process is carried out exactly like the first coupling, including washing procedure and drying, the only modification being that here the terminal alkyne is generated beforehand by deprotection with tetrabutylammonium fluoride (TBAF) in THF and added after substantial removal of the solvent under high vacuum.

The following amounts were used:

Resin-bound 4-iodobenzamnide (500 mg; 0.25 mmol); Pd(PPh$_3$)$_2$Cl$_2$ (17.5 mg; 0.025 mmol); CuI (11.9 mg; 0.063 mmol); toluene (5 ml); diethylamine (5 ml); 2-trimethylsilylethynylaniline (475 mg; 2.5 mmol); TBAF (11.0 ml, 2.75 mmol).

The resulting intermediate was then cyclized to give the indole, as follows:

The polymer-bound starting material (200 mg; 0.09 mmol) was initially charged in a Schlenk tube, fitted with septum and filled with argon, and swollen in NMP (4 ml) for about 5 min. The mixture was then cooled to 0° C., and a solution of KOtBu (150 mg; 1.35 mmol) in NMP (12 ml) was added dropwise. The mixture was then stirred at room temperature for 24 h, and the resin was filtered and washed with dichloromethane, THF, methanol, DMF (in each case about 5 ml). The washing procedure was repeated about ten to twelve times. The polymer was then washed four times with dichloromethane (in each case about 5 ml) and dried at 55° C. for about 16 h.

The resulting resin was then cleaved using TFA/dichloromethane 1:1.

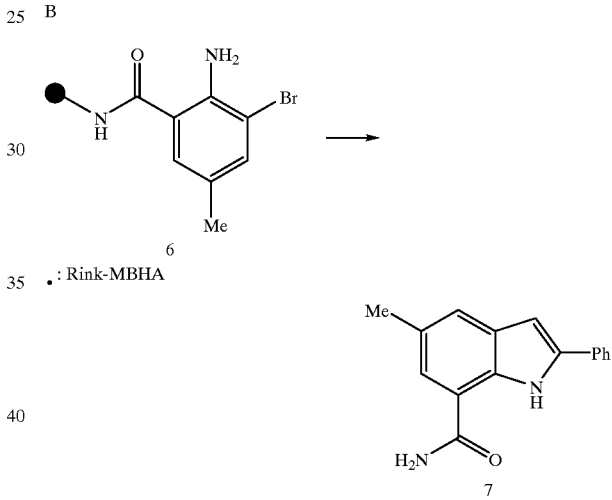

• : Rink-MBHA

The Sonogashira coupling was carried out as described above under A, but at 80° C. over the course of 18 h, and the starting material used was resin-bound 2-bromo-4-methylaniline. 50 mol % of CuI were used. The reaction with KOt-Bu was then carried out by method A, as was the cleavage of the resin.

We claim:

1. A process for preparing compounds of the indole type of the formula

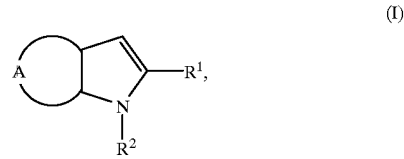

in which A is a hydrocarbon radical which, together with the carbons to which it is attached, forms a substituted or unsubstituted mono- or polycyclic aromatic system which does or does not contain one or more heteroatoms from the group consisting of N, O and S, and R$^1$, R$^2$ independently of one another are H, a saturated, linear or branched aliphatic $C_1$–$C_{20}$-hydrocarbon radical, an unsaturated, linear or branched aliphatic $C_2$–$C_{20}$-hydrocarbon radical, a saturated or unsaturated, unsubstituted or alkyl-substituted cycloaliphatic $C_3$–$C_{20}$-hydrocarbon radical or an aromatic $C_5$–$C_{20}$-hydrocarbon radical, where these radicals optionally contain in their molecular skeleton one or more heteroatoms from the group consisting of the halogens, N, P, O, S, Si, Sn and B and is or is not substituted or unsubstituted, which comprises cyclizing of alkynylaminoaromatics of the formula

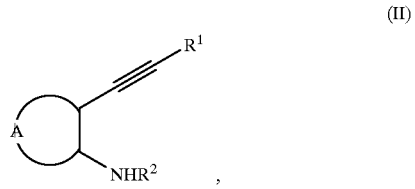

(II)

in which $R^1$ and $R^2$ are as defined in formula (I) and $R^1$, $R^2$ or A is optionally attached to an organic or inorganic carrier, in a polar aprotic ion-solvating solvent in the presence of a compound of Na, K, Rb or Cs which dissociates well in the solvent mentioned and whose ions are sufficiently solvated by the solvent compound of Na, K, Rb or Cs.

2. A process as claimed in claim 1, wherein the substituents $R^1$ and $R^2$ independently of one another are selected from the group consisting of H, linear and branched $C_1$–$C_{12}$-alkyl groups, linear and branched $C_2$–$C_{12}$-alkenyl groups, $C_3$–$C_8$-cycloalkyl groups, $C_3$–$C_8$-cycloalkenyl groups, $C_5$- and $C_6$-heterocycles having one or more ring atoms selected from the group consisting of N, O and S and mono- or bicyclic aromatics having one or more ring atoms selected from the group consisting of N, O and S.

3. A process as claimed in claim 1, wherein the hydrocarbon groups defined for $R^1$ and $R^2$ carry one or more substituents selected from the group consisting of amino and nitro groups, halogens, hydroxyl and ether groups, thiol groups, thioether groups, amide and ester groups, sulfaryl groups and sulfoxide groups.

4. A process as claimed in claim 1, wherein a hydride, hydroxide, alkoxide, amide or aminopropylamide of Na, K, Rb or Cs is used.

5. A process as claimed in claim 1, wherein the solvent used is N-methylpyrrolidone, N-butylpyrrolidone, dimethyl sulfoxide, sulfolane, dimethylformamide, tetrahydrofuran, hexamethylphosphoric triamide, N,N'-dimethylpropyleneurea or an ether, or a mixture of these solvents.

6. A process as claimed in claim 1, wherein the aromatic system in the compound of the formula (I) is a substituted or unsubstituted mono- or bicyclic aromatic, preferably a substituted or unsubstituted aromatic selected from the group consisting of $C_5$-heterocycles, benzene and naphthalene derivatives.

7. A process as claimed in claim 1, wherein the alkali metal compound is employed in an amount of from 5 mol % to 150 mol %, based on the substrate.

8. A process as claimed in claim 1, wherein the process is carried out at temperatures <100° C.

9. A process as claimed in claim 1, wherein the reaction time is from 2 to 20 hours, preferably from 2 to 8 hours.

10. A process as claimed in claim 1, wherein the alkynylaminoaromatic (II) used as starting material is attached to an organic or inorganic carrier, preferably selected from the group consisting of Merrifield resin, rink-MHBA resin and trityl chloride resin, if appropriate after appropriate modification, and immobilized, and the bond between carrier material and target molecule is broken in a manner known per se when the synthesis has ended.

11. The process of claim 1 which is carried out in the presence of a compound of K or Cs which dissociates well in the solvent mentioned and whose ions are sufficiently solvated by the solvent.

12. The process of claim 5 wherein the solvent is N-methylpyrro- lidone, N-butylpyrrolidone, diemthyl sulfoxide, sulfolane, dime- thylformamide, tetrahydrofuran, hexamethylphosphoric triamide, N,N'-dimethylpropyleneurea or an ether prepared from ethylene ox- ide and/or propylene oxide or from ethylene oxide and propylene oxide and a polyvalent amine, or a mixture of these solvents 13. The process of claim 6 wherein the aromatic system in the compound of formula (I) is a substituted or unsubstituted mono- or bicyclic radical selected from the group consisting of ben- zene, naphthalene, pyridine, pyrazine, pyrimidine, quinoline, thiophene and furan.

14. The process of claim 8 wherein the temperature is from 20 to 60° C.

15. The process of claim 8 wherein the temperature is from 20 to 40° C.

16. The process of claim 9 wherein the reaction time is from 2 to 8 hours.

* * * * *

UNITED STATES PATENT AND TRADEMARK OFFICE
CERTIFICATE OF CORRECTION

PATENT NO. : 6,384,235 B2
DATED : May 7, 2002
INVENTOR(S) : Henkelmann et al.

It is certified that error appears in the above-identified patent and that said Letters Patent is hereby corrected as shown below:

Column 11,
Line 36, "carry" should be -- are substituted by --.

Column 12,
Line 13, delete ", preferably from 2 to 8 hours".
Line 28, "N-methylpyrro- lidone" should be -- N-methylpyrrolidone --.
"diemthyl" should be -- dimethyl --.
Line 29, "dime- thylformamide" should be -- dimethylformamide --.
Line 32, "ox- ide" shoud be -- oxide --.
Line 38, "ben- zene" should be -- benzene --.

Signed and Sealed this

Tenth Day of September, 2002

Attest:

JAMES E. ROGAN
Attesting Officer
Director of the United States Patent and Trademark Office